United States Patent [19]

Sakamoto

[11] Patent Number: Plant 6,924

[45] Date of Patent: Jul. 18, 1989

[54] HYDRANGEA PLANT NAMED KUMIKO

[75] Inventor: Shoji Sakamoto, Ohaza Shimotazawa Kurohone, Japan

[73] Assignee: Sakata Seed America, Inc., Morgan Hill, Calif.

[21] Appl. No.: 226,997

[22] Filed: Aug. 1, 1988

[51] Int. Cl.[4] ..... A01H 5/00

[52] U.S. Cl. ..... Plt./54

[58] Field of Search ..... Plt./54

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new variety of Hydrangea named Kumiko, producing large clusters of purplish pink flowers suitable for growing outdoors or in pots.

2 Drawing Sheets

The present invention relates to a new and distinct variety of Hydrangea plant which was originated by me as a selected seedling derived by crossing as male and female parents respectively the varieties known as "Grunherz" and "Madam Plumecoq". The botanical name for this plant is *Hydrangea hortensia* Sm. The varietal denomination of this new Hydrangea is Kumiko.

The breeding program of the inventor resulting in the new variety had the primary object of creating a variety of Hydrangea possessing large flower size in combination with plant growth habit suitable for both outdoor garden usage as well as for growing in pots. The new variety as described herein additionally possesses excellent plant habits, strong stems, attractive large purplish pink flowers, and excellent clustering quality. My new variety of hydrangea is capable of blooming in outdoor plantings during the months of June and July as well as flowering in greenhouses in the months of March and April. When grown in greenhouses, flowering is approximately 10 to 11 months after rooting of cuttings.

Among the novel characteristics possessed by this new variety of Hydrangea which distinguish it from its parents and all other varieties of which I am aware are its substantially stable purplish pink flowers of a shade between the darker colored flowers of parent Grunherz and the paler colored flowers of its seed parent Madam Plumecoq, and its large flower size and more vigorous plant habit.

Kumiko originated from a hybridization made by the inventor in a controlled breeding program in Gunma-Pefecture, Japan. The female, or seed, parent of Kumiko was Madam Plumecoq. The male or pollen parent of the new variety was Grunherz. Kumiko was discovered and selected as one flowering plant within the progeny of the stated parentage by me in a controlled environment.

The first act of asexual reproduction of Kumiko was accomplished when vegetative cuttings were taken by the inventor from the initial selection in a controlled environment. Horticultural examination of selected units in March and April has demonstrated that the combination of characteristics as herein disclosed for Kumiko are firmly fixed and are retained through successive generations of asexual reproduction.

Kumiko has not been observed under all possible environmental conditions. The phenotype may vary significantly with variations in environment such as temperature, light intensity and day length. The following observations, measurements and comparisons describe plants grown in Gunma-Prefecture, Japan under greenhouse conditions which approximate those generally used in commercial practice.

The accompanying photographic drawings show typical plant specimens of the new cultivar, with colors being as true as possible with color illustrations of this type. The photograph at the top of Sheet 1 is a front perspective view of Kumiko. The photograph at the bottom of Sheet 1 illustrates Kumiko, on the right, and the parent cultivars Grunherz and Madam Plumecoq. The photograph at the top of Sheet 2 is a comparison view of a single leaf and petal of Kumiko and the parent cultivars. The photograph at the bottom of Sheet 2 is a closeup of the petals of Kumiko, with the petal color being somewhat lighter than the true petal color described below.

The following is a detailed description of my new variety, with color references being to the Royal Horticultural Society (RHS) Colour Chart).

Parentage:

*Seed parent.*—"Madam Plumecoq".

*Pollen parent.*—"Grunherz".

*Classification.*—*Hydrangea hortensia* Sm.

Plant:

*Habit.*—Vigorous, well branched.

*Height attained.*—About 15 inches.

*Width.*—About 20 to 22 inches.

*Foliage.*—Size — average. Quantity — abundant. Color — dark green upper surface, near 141A. Shape — acuminate. Texture — dull. Stems — strong, erect aspect.

Flowers:

*Flowerhead.*—Terminal, composite, globular; composed of florets carried on sturdy peduncles.

*Size.*—Flower size about 2.3 to 2.5 inches.

*Petalage.*—4 to 5 petals.

*Flower cluster.*—10 to 12 inches, with clusters being immediately above foliage.

*Color.*—Near to 65B, very stable.

Blooming period:

*Outdoors.*—June to July, full sun.

*Greenhouse.*—March to April.

Reproductive organs:

*Filaments and anthers.*—Ivory color.

*Styles.*—Short.

*Pollen.*—Lavender.

*Ovaries.*—Ovoid, pale yellow.

Propagation: By vegetative cuttings, flowering occurring 10 to 11 months after rooting under greenhouse culture.

I claim:

1. A new and distinct variety of Hydrangea plant, named Kumiko, substantially as shown and described herein.

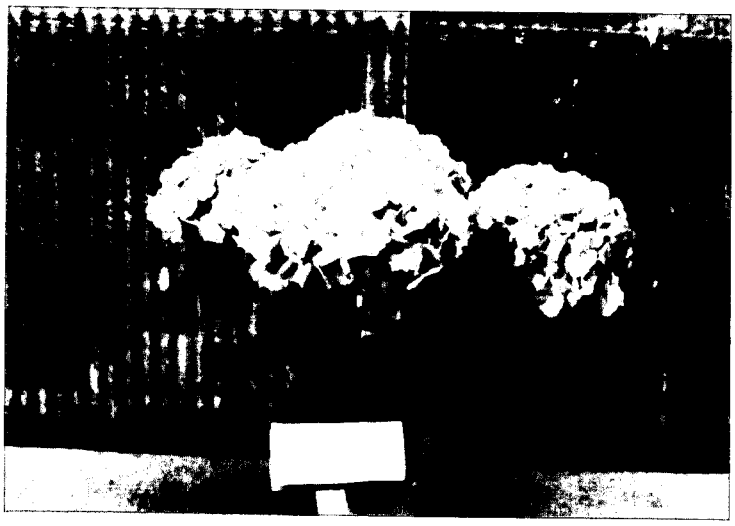
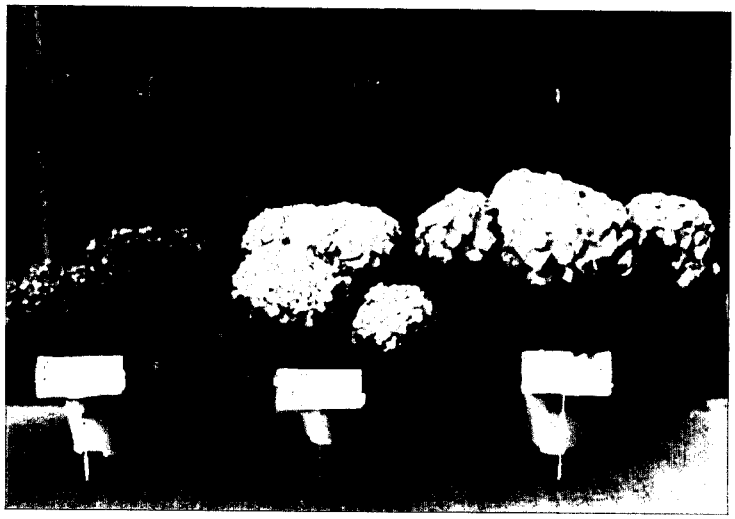

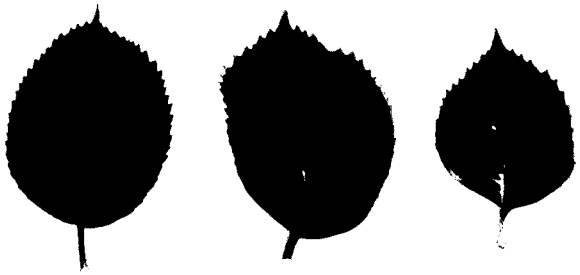
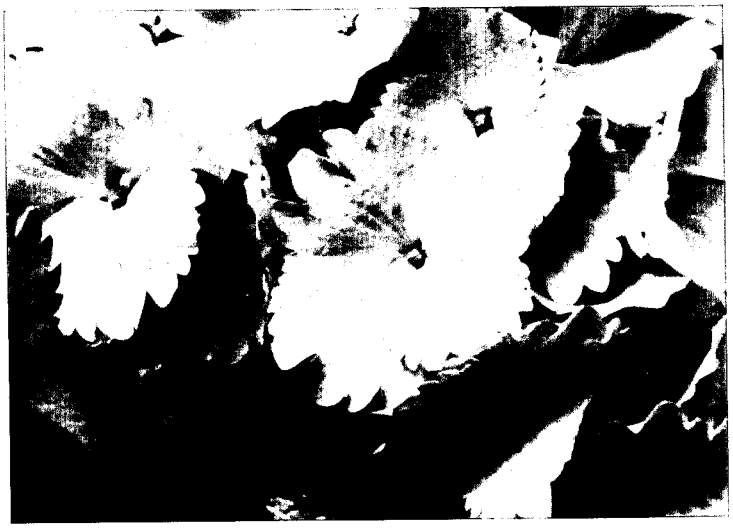

* * * * *